United States Patent [19]

Baragar et al.

[11] 4,332,160
[45] Jun. 1, 1982

[54] PENETROMETER

[76] Inventors: Harold A. Baragar, 311 Wascana Rd. SE.; Kenneth S. Toovey, 5947 Dalhousie Dr. NW., both of Calgary, Alberta, Canada

[21] Appl. No.: 137,985

[22] Filed: Apr. 7, 1980

[30] Foreign Application Priority Data

Apr. 19, 1979 [AU] Australia ............................. PD8473

[51] Int. Cl.³ .............................................. G01N 3/00
[52] U.S. Cl. ...................................... 73/84; 73/862.38
[58] Field of Search ....................... 73/84, 862.38, 151

[56] References Cited

U.S. PATENT DOCUMENTS

| 1,860,932 | 5/1932 | Lamb | 73/151 UY |
| 2,466,034 | 4/1949 | Mathews | 73/141 A |
| 3,968,682 | 7/1976 | Pellissier | 73/84 |
| 3,988,923 | 11/1976 | Elmiger et al. | 73/84 |
| 3,999,424 | 12/1976 | Pellissier | 73/84 X |

Primary Examiner—Jerry W. Myracle
Attorney, Agent, or Firm—Stanley G. Ade

[57] ABSTRACT

A static-dynamic penetrometer consists of a cone tip secured to the end of one or more coupled rods and is attached to the lower end of a conventional drill rig assembly and is applied initially in a manner similar to that of the Standard Penetration Test (ASTM:D 1586). A load cell component containing an internaly gauged strain stud is then installed in series at the drill head so that the total applied load can be read on an electric readout device such as an electric analog load-indicator. The necessary reaction for "quasi-static" or "static" loads is supplied by the drill rig. Skin fraction may be measured statically and quasi-statically by withdrawal procedures and this and point bearing loads may be estimated from the data thus obtained.

19 Claims, 6 Drawing Figures

PENETROMETER

This invention relates generally to a measuring device such as a probe for conducting measurements into soil substrata into which the probe is driven or pushed. It is concerned with a measuring probe for measuring skin friction and point pressure in a substratum.

Devices of this general type are widely used for determining the characteristics of soil strata at depths below the earth's surface. They employ a probe which is forced into the substrata and which is provided with measuring devices so that the use of such a probe can make deductions concerning the engineering strength characteristics of the soil strata, the consistency and the layering thereof, from the force required to push the probe body through the soil and, in the case of the subject penetrometer, withdraw same after penetration.

The total force acting upon the pressure measuring device of the probe is composed of the force acting lengthwise of the probe upon the tip at the leading end thereof and the skin friction acting upon surface portions of the probe in contact with the soil, and when these measurements are known, conclusions may be drawn concerning the soil characteristics, and any changes of soil characteristics from a looser to a more dense stratum or vice versa.

Measuring devices are well known for this purpose but they all suffer from disadvantages which include sophisticated and/or delicate instrumentation adjacent to or within the probe tip which may be easily damaged.

One of the principal advantages of the present device is its simplicity of design and operation inasmuch as there is almost no sophisticated apparatus that can offer opportunities for error or failure inasmuch as the design is extremely rugged.

The majority of existing apparatus that permit reading of point bearing and skin friction include various kinds of sensitive instrumentation placed within the penetrometer body which has then to be driven or pushed at depth into the ground.

With the present device, the strain gauged stud and "read out" load indicator remain above ground so that all that is inserted into the ground is an approximately 2 inch diameter penetrometer on the end of a drill rod.

The penetrometer operation can be incorporated in a conventional geotechnical investigation type of drilling/ or augering and/or sampling program so that all conventional types of sampling and in-situ testing may be carried out within the same bore hole if so desired.

The penetrometer may also be used as a dynamic penetrometer and can replace the commonly known Standard Penetration Test (ASTM:D 1586). Correlation with this test to-date indicates approximately a 1:1 ratio when driven to the same depth of penetration with all other standard equipment.

One significant advantage is that samples can be obtained as required through application of standard investigational bore hole sampling procedures. Other static/ dynamic type penetrometers are simply forced or driven from ground surface generating only sufficient cavity size for their own passage and generally recovering no samples for visual laboratory or other evaluations.

A further difficulty with conventional penetrometers which provide a cavity only for their own passage, is that difficult driving/pushing conditions may completely stop progress downwardly and this may be caused by a relatively thin layer of highly resistant material.

The present device, in such a situation, may be withdrawn and the hole advanced by augering or drilling and the penetrometer may then be replaced in the hole for further exploration at depth. This can be of great significance if a less competent layer of soil underlies a thin but resistent layer such as shale, gravel, cobbles or small boulders.

The so-called "Dutch Cone" (a well known standard tool much used in Europe and world-wide) encounters this problem at very shallow depths if gravel, cobbles or boulders are encountered.

These conditions are very common to "till" soils which are common to at least the northerly half of the American continent, parts of Britain and Europe. Using the present penetrometer and standard bore hole drillng techniques, obstructions may be by-passed and readings obtained at further depths.

No cables, wires, proving rings, push-rods, tubes or push-rods within tubes, or hydraulic hoses or gauges are required to operate the equipment or obtain readings; and none of this delicate equipment is contained in the penetration tip as is the case with almost all other penetrometers.

We have provided a simple penetrometer and friction measuring apparatus which will provide an in-situ evaluation of the soil parameters necessary for an adequate and economical design for all types of piles and more specifically for driven piles for both end-bearing and ski-friction capacities. In accordance with the invention there is provided a penetrometer assembly for use with a reaction producing device such as a drill rig or the like, having a connecting rod depending from the drill head thereof and an electric readout device; comprising in combination a penetrometer rod, a penetration tip on one end thereof and a load cell component operatively connected in series with the other end thereof, said load cell component including a housing and a strain gauged stud mounted therein for actuation by tension or compression loads upon said penetration rod and tip thereon.

In another aspect of the invention there may be provided a load cell component for use with the penetrometer assembly comprising in combination a housing and a strain gauged stud mounted therein for activation by tension or compression forces acting thereon, said housing including a lower end portion, a central sleeve portion and an upper end portion, the lower end of said central sleeve portion slidably engaging with the upper end of said lower end portion, said upper end portion being detachably connected to the upper end of said central sleeve portion, said strain gauged stud being operatively connected between said central sleeve portion and said lower end portion.

A further aspect of the invention consists of a method of estimating the characteristics of subsoil strata consisting of the steps of advancing a bore hole to the desired elevation, installing a penetrometer rod assembly and cone tip on the apparatus (drill rods) used to advance the bore hole, driving the penetrometer rod and tip a predetermined distance into the strata using Standard Penetration Test procedures (ASTM:D 1586) and ascertaining the N-value of the strata, installing a load cell component in series upon the outer end of the penetrometer rod assembly, operatively connecting the load cell component to an electric readout indicator, applying a sufficient compression loading to the penetrometer rod assembly to cause the penetrometer rod assembly and cone tip to penetrate the strata at a predetermined rate, down to practical refusal, and then recording the maximum applied compression as measured, applying tension loading on the penetrometer rod assembly and reading the maximum pull required to initiate withdrawal of the penetrometer rod assembly and continuing or sustaining the tension loading to cause withdrawal and recording the pull required to withdraw the penetrometer rod assembly.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

In the drawings like characters of reference indicate corresponding parts in the different figures.

Figure 1:
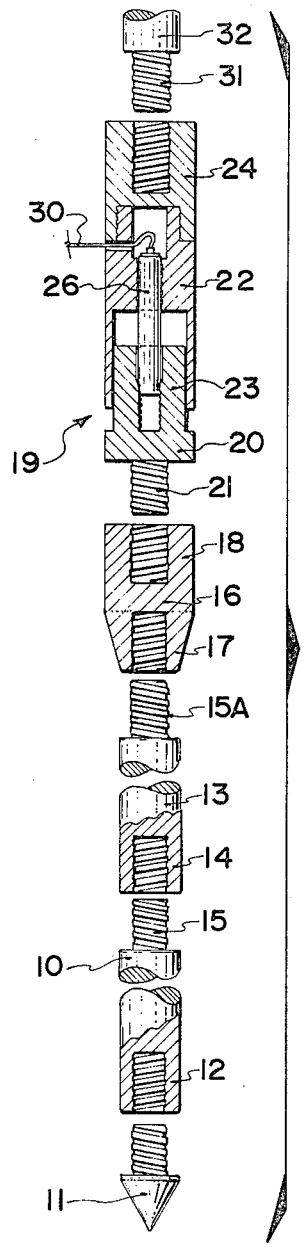
FIG. 1 is a partially exploded and partially sectioned schematic side elevation view of the penetrometer.

Proceeding therefore to describe the invention in detail, the tool consists of a penetrometer rod such as a steel rod 10 of approximately two inches diameter and a length of approximately five feet. A penetration tip 11 which is conical, is screw threadably engageable within the lower end 12 of the rod 10 and although the single penetrometer rod 10 may be sufficient, it can be extended by the use of one or more extension rods 13 screw threadably engageable by lower end 14 to the male threaded upper end 15 of the main rod 10. Alternatively, one or more lengths of conventional drill rod (not illustrated) may be used to provide the necessary connection to the penetrometer rod depending upon the depth at which the measurements are to be taken and it should be understood that the term "penetrometer rod" includes one or more lengths of penetrometer rod such as that illustrated by reference characters 10 or 13.

Figure 4:
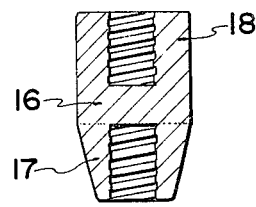
FIG. 4 is a cross sectional elevational view of the coupling connection box per se.

A coupling connection box is shown in FIG. 4 and identified by reference character 16. This is a short cylindrical component having a female screw threaded lower end 17 engageable with the upper end 15 of the rod 10 or 15A of the extension 13 or of the drill rod (not illustrated). The female screw threaded upper end 18 of the connection box, is engaged by a load cell component collectively designated 19 and shown in detail in FIG. 2. This is an assembly which includes a lower end portion 20 having the screw threaded lower end 21 engageable within the coupling portion 18 of the connection box 16, a central sleeve portion 22 slidably engageable at its lower end over the cylindrical body 23 of the lower end portion 20, and an upper end portion 24 screw threadably engageable over the upper end 25 of the sleeve portion 22. The sleeve portion carries a strain gauged stud 26 screw threaded by the upper end thereof into a concentric bore through the main body of the sleeve portion as at 27 and screw threadably engageable by the lower end portion 28, within a concentric bore through the lower end portion 20 of the load cell as indicated by reference character 29.

An electric connecting cable 30 extends from the strain gauged stud to a battery-operated read out shown schematically by reference character 30A. A suitable readout is a modified Strainsert Model PLN-1 portable analog load indicator.

Although various types of strain studs may be used, an example of a satisfactory stud is manufactured by the Strainsert Company of Pennsylvania, U.S.A., and details of such studs are discussed in U.S. Pat. No. 2,873,341.

A suitable example of such studs is a strain stud 0.785" ($\frac{7}{8}$") diameter Strainsert type W internally gauged SJ-Q $\frac{7}{8}$" 9 N.C. -6 (120 OHM 150 F.DEG) W-To-Ko-So, S/N-1.

As the construction and operation of such studs is well known, it is not believed necessary to discuss same further except to state that a certain type of stud is defined as is the portable analog load indicator. However, it should be stressed that these are examples only and equivalent parts can be used.

The upper end portion 24 of the load cell is screw threadably engageable with the lower screw threaded male end 31 of a relatively short connecting rod 32, which extends to the drill head of the drill rig (not illustrated) all above the ground surface.

The preferred method of operation for the penetrometer utilizes a conventional mobile-auger type drill rig or the equivalent (not illlustrated) and is as follows:

Firstly, the bore hole is advanced to the desired elevation by means of the drill rig and then the penetrometer assembly is installed in place of the auger or at the bottom of the drill stem (not illustrated) or inside a hollow stem auger (not illustrated) at the lower end of the drill rod 32, but without the load cell 19 installed, and in this connection, the coupling connection box 16 shown in FIG. 4 is engaged instead of the load cell structure.

If the soil is estimated to be "stiff" or "dense" then the approximately five-foot length of penetrometer 10 together with the cone tip 11 may be all that is required. However, if the soil is estimated to be "soft" or "loose" then two or more approximately five-foot extensions 13 may be added. If the depth to the stratum to be tested is considerable, conventional drill rod may be used.

The penetrometer may then be driven dynamically to a penetration of approximately 18 inches (as for the Standard Penetration Test)(ASTM:D 1586) and utilizing the Standard Penetration Test driving equipment, i.e. 140 pound hammer and a 30 inch drop. In this connection, the number of blows required to drive the penetrometer for each 6 inch increment of penetration are counted and the number of blows to drive the penetrometer the last 12 inches being designated as the "N"-value for this penetrometer in that particular soil.

The N-value thus obtained may be compared with a comparative N-value obtained from a Standard Penetration Test device in the same stratum in other nearby holes or immediately above or below the present penetrometer N-value test in the same hole. Similar correlations to-date have indicated that the values are equivalent or on a 1:1 ratio.

Figure 2:
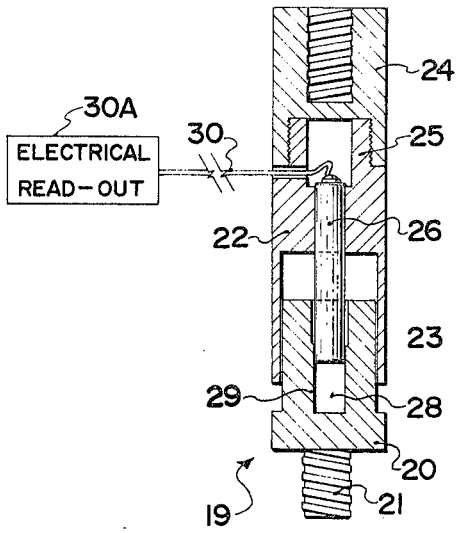
FIG. 2 is a partially cross sectional view showing schematically, details of the load cell with the strain stud installed therein.
Figure 3:
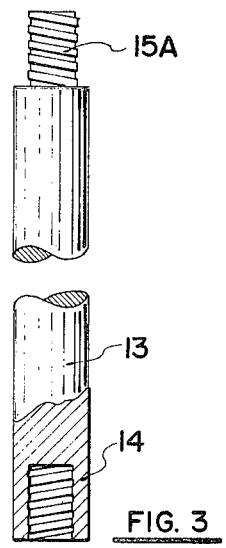
FIG. 3 is a fragmentary detailed view of the extension rod.

The entire load cell 19 component shown in FIG. 2 including strain stud 26 is now installed at the top of the drill rod or penetrometer rod 10 and/or extension(s) 13 as shown in FIG. 1, at the ground surface, and connected to the read-out 30A also at the surface. With no load on the penetrometer, the read-out is zeroed on the "compression" scale and a very light initial load in compression is applied sufficient only to visibly deflect the read-out needle. The load is then removed and the read-out is once again zeroed if necessary.

The portable analog load indicator is now set with the function on "Q" and the "range" at a previously calibrated setting approximating 2.31. "Balance" is used to zero for readings in tension at the left hand side of the scale or compression at the right hand side of the scale and the zeroing is re-checked.

Compression loading is now applied to the drill rod 32, relatively slowly thus causing the penetrometer to penetrate the strata at a rate of less than 1 cm per second (approximately ½ inch per second).

The total applied force is read at the end of each one foot interval of penetration or other preselected intervals. The application of load should be stopped momentarily if necessary at the end of each selected interval and the maximum applied force recorded. The application of force is resumed with maximum penetration rate of 1 cm per second (approximately ½ inch per second) and continued readings at selected (one foot) intervals are taken and recorded as before, down to practical refusal at maximum load capability of the drill rig. The total penetration is recorded for the penetrometer and the load is held at the refusal loading for a minimum of 30 seconds. Care should be taken that the total length of the 2 inch diameter penetrometer rods and extensions is not exceeded in total penetration. If desired, this operation may be carried out as a continuous penetration to practical refusal without stops with the load at each interval being read instantaneously.

The next step is to prepare to withdraw the penetrometer. With no load on the penetrometer, zero the readout at 0 (LHS) on "tension" scale. A very light initial load is applied in tension sufficient only to visibly deflect the read-out needle and this load is then removed and the meter is re-zeroed if necessary.

The tension loading is then applied very slowly to the drill rod and the maximum pull (tension) is read which is required to initiate withdrawal with little or no upward movement occurring, and this "peak" tension load is recorded.

The "residual" pull (tension) is then read, the residual pull being that pull required to continue withdrawal immediately after the maximum "peak" pull has been recorded. This residual tension load should also be recorded.

Further "residual" pull which is required for continued withdrawal is then read and recorded at the lower limit of each of the same selected intervals as read during penetration (compression). The pull should be stopped momentarily while each reading is taken and recorded. This operation also may be carried out, if desired, as a continuous withdrawal without stops with the load at each interval being read instantaneously.

It should be stressed that the maximum "peak" pull and the residual pull must be taken in rapid succession. The first, essentially before any measurable upward movement has occurred, and the second within the initial 1/16th inch of upward movement of the penetrometer. Hence, close attention during the taking of these two readings is obviously very essential.

The penetrometer is then withdrawn from its penetration hole only and the upward lift is stopped. The static weight of the drill rod and penetrometer is read and recorded whereupon the load cell can be removed and the penetrometer also withdrawn and removed.

Corrected loadings are calculated as follows:
(a) In Compression:
Total Push=(load reading)+(static weight of drill rod and penetrometer).
(b) In tension:
Total pull [for either "peak" (static) or "residual" (quasi-static)]=(load reading)−(static weight of drill rod and penetrometer).

"Peak" (static) or "residual" (quasi-static) values of skin friction loads may be calculated as in (b) above.

Point bearings for cone tip=(a) above-(b) above for "peak" or static pull, i.e. the difference between maximum push (compression) load and "peak" pull (tension) load.

Surface area of penetrometer=0.5236 sf/lf; unit skin friction may be calculated as follows:

$$\frac{\text{Corrected Total "Peak/Residual" (Static/Quasi-Static) Load}}{\text{Depth of Penetration} \times 0.5236} ;$$

psf.

Effective end area of penetrometer tip=0.0218 sf.
Unit point bearing for penetrometer may be calculated as follows:

$$\frac{\text{Corrected Total Point Bearing}}{0.0218} ; \text{psf.}$$

Bearing capacity: The relationship of ultimate penetrometer unit tip resistance to ultimate bearing capacity for spread foundations or ultimate end-bearing capacity for piles is presently assumed to be calculated by multiplying by some constant K (to be determined);
$q_{ult}=Kq_p$; $q_p$=ultimate unit point resistance penetrometer. All units may be in psi, psf or KPa.

This will require confirmation by full-scale load tests on piles or spread foundations.

Skin friction: Ultimate unit skin friction for a driven pile in a given stratum is presently assumed to correlate on a 1:1 basis with the unit skin friction determined from the penetrometer test—either "peak" (static) or "residual" (quasi-static). This will also require confirmation by full-scale load tests on piles.

Figure 6:
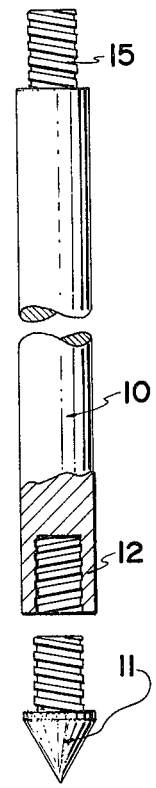
FIG. 6 is an exploded, partially broken away, detailed elevational view of the penetrometer and penetration tip.

To obtain greater penetrations for purposes of determination of an average unit skin friction value over a greater length of penetrometer shaft than can be pushed to refusal by the available reaction (drill rig), use the following procedure:

(a) Remove the complete load cell component 19 (in FIG. 2), and reconnect the drill rod and/or penetrometer rod(s). Drive the penetrometer and tip 10 and 11 (in FIG. 6), beyond static refusal depth by the dynamic method (as for the Standard Penetration Test (ASTM:D 1586).

(b) After dynamic refusal is met, re-install the load cell and read "peak" (static) and "residual" (quasi-static) friction pull-out (tension loads for penetrometer as instructed hereinbefore.

Total penetration of the penetrometer using the dynamic method must be limited to the total length of 2 inch diameter penetrometer and extensions in use at that time.

Figure 5:
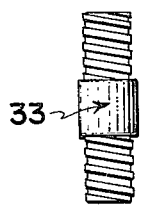
FIG. 5 is an elevational view of a coupling per se.

FIG. 5 shows a male screw threaded coupling 33 which may be used to connect to rod 32 if a female coupling is provided thereon or for any other needed connection for the various rods and components which may be encountered.

Since various modifications can be made in my invention as hereinabove described, and many apparently widely different embodiments of same made within the spirit and scope of the claims without departing from such spirit and scope, it is intended that all matter contained in the accompanying specification shall be interpted as illustrative only and not in a limiting sense.

The claims defining the invention are as follows:

We claim:

1. A penetrometer assembly for use with a reaction producing device such as a drill rig or the like, having a connecting rod depending from the drill head thereof and an electric readout device for penetration and withdrawal into and from a substratum; comprising in combination a penetrometer rod, a penetration tip on one end thereof and a load cell component operatively connected in series with the other end thereof and remote from said one end of said rod, said load cell component remaining above the substratum and including a housing and a strain gauged stud mounted therein for actuation by tension or compression loads upon said penetration rod and tip thereon, said housing including a lower end portion, a central sleeve portion and an upper end portion, the lower end of said central sleeve portion slidably engaging with the upper end of said lower end portion, said upper end portion being detachably connected to the upper end of said central sleeve portion, said strain gauge stud being operatively connected between said central sleeve portion and said lower end portion.

2. The invention according to claim 1 which includes a coupling connector box screw threadably engaged between the upper end of said penetration rod at one end of said housing, said connector box including a body having screw threaded female bores axially situated in each end thereof.

3. The invention according to claim 2 in which said housing includes a lower end portion, a central sleeve portion and an upper end portion, the lower end of said central sleeve portion slidably engaging with the upper end of said lower end portion, said upper end portion being detachably connected to the upper end of said central sleeve portion, said strain gauged stud being operatively connected between said central sleeve portion and said lower end portion.

4. The invention according to claim 3 in which said lower end portion includes an axial screw threaded bore extending from the upper end thereof towards but terminating spaced from the lower end thereof, said strain gauged stud screw threadably engaging said bore by one end thereof, said central sleeve portion including an axially situated hollow portion defining a shell at the lower end thereof slidably engaging over said lower end portion and a screw threaded axial bore extending through said upper end portion of said central sleeve portion, said strain gauged stud screw threadably engaging said last mentioned axial bore, by the other end thereof.

5. The invention according to claim 4 in which the upper end of said upper end portion screw threadably engages the lower end of the associated connecting rod.

6. The invention according to claim 5 in which said penetration tip is screw threadably engageable within said penetration rod and is conical in configuration.

7. The invention according to claim 3 in which the upper end of said upper end portion screw threadably engages the lower end of the associated connecting rod extending from the drill head.

8. The invention according to claims 1 or 2 in which said penetration tip is screw threadably engageable within said penetration rod and is conical in configuration.

9. The invention according to claim 1 in which said lower end portion includes an axial screw threaded bore extending from the upper end thereof towards but terminating spaced from the lower end thereof, said strain gauged stud screw threadably engaging said bore by one end thereof, said central sleeve portion including an axially situated hollow portion defining a shell at the lower end thereof slidably engaging over said lower end portion and a screw threaded axial bore extending through said upper end portion of said central sleeve portion, said strain gauged stud screw threadably engaging said last mentioned axial bore, by the other end thereof.

10. The invention according to claims 3, 9 or 4 in which said penetration tip is screw threadably engageable within said penetration rod and is conical in configuration.

11. The invention according to claim 9 in which the upper end of said upper end portion screw threadably engages the lower end of the associated connecting rod extending from the drill head.

12. The invention according to claim 1 in which the upper end of said upper end portion screw threadably engages the lower end of the associated connecting rod extending from the drill head.

13. The invention according to claims 12, 7 or 11 in which said penetration tip is screw threadably engageable within said penetration rod and is conical in configuration.

14. A method of measuring engineering strength characteristics of subsoil strata consisting of the steps of advancing a bore hole to the desired elevation, installing a penetrometer rod assembly and cone tip on the apparatus (drill stem) used to advance the bore hole, driving the penetrometer rod and tip a predetermined distance into the strata using Standard Penetration Test procedures (ASTM:D 1586) and ascertaining the N-value of the strata, installing a load cell component in series upon the upper end of the penetrometer rod assembly, operatively connecting the load cell component to an electric readout indicator, applying a sufficient compression loading to the penetrometer rod assembly to cause the penetrometer rod assembly and cone tip to penetrate the strata at a predetermined rate, down to practical refusal, and then recording the maximum applied compression as measured, applying tension loading on the penetrometer rod assembly and reading the maximum pull required to initiate withdrawal of the penetrometer rod assembly and continuing the tension loading so as to cause withdrawal and recording the pull required to withdraw the penetrometer rod assembly.

15. The method according to claim 14 which includes the additional steps of staging the driving or pushing and withdrawal of the penetrometer rod assembly at predetermined increments and recording the compression loading and tension loading respectively at said predetermined increments.

16. The method according to claim 15 in which the rate of penetration and withdrawal does not exceed approximately ½" per second.

17. The method according to claim 14 in which the rate of penetration and withdrawal does not exceed approximately ½" per second.

18. A load cell component for use with a penetrometer assembly comprising in combination a housing and a strain gauged stud mounted therein for activation by tension or compression forces acting thereon, said housing including an upper end portion, a central sleeve portion connected to the lower end of said upper end portion and a separate, independent lower end portion slidably engageable within the lower end of said central sleeve portion, said strain gauged stud being operatively connected between said central sleeve portion and said lower end portion.

19. The invention according to claim 18 in which said lower end portion includes an axial screw threaded bore extending from the upper end thereof towards but terminating spaced from the lower end thereof, said strain gauged stud screw threadably engaging said bore by one end thereof, said central sleeve portion including an axially situated hollow portion defining a shell at the lower end thereof slidably engaging over said lower end portion and a screw threaded axial bore extending through said upper end of said central sleeve portion, said strain gauged stud screw threadably engaging said last mentioned axial bore, by the other end thereof.

* * * * *